(12) United States Patent
McDevitt

(10) Patent No.: US 6,280,768 B1
(45) Date of Patent: Aug. 28, 2001

(54) BERBERINE ALKALOIDS AS A TREATMENT FOR CHRONIC PROTOZOALLY INDUCED DIARRHEA

(75) Inventor: Joseph T. McDevitt, Villanova, PA (US)

(73) Assignee: PRM Pharmaceuticals, Inc., Ardmore, PA (US)

(*) Notice: Subject to any disclaimer, the term of this patent is extended or adjusted under 35 U.S.C. 154(b) by 0 days.

(21) Appl. No.: 08/886,827

(22) Filed: Jul. 1, 1997

Related U.S. Application Data

(60) Provisional application No. 60/019,821, filed on Jul. 3, 1996.

(51) Int. Cl.⁷ .............................. A61K 9/16; A61K 9/20; A61K 9/48
(52) U.S. Cl. .................... 424/464; 424/451; 424/489; 514/867; 514/280
(58) Field of Search ................................. 424/464, 451, 424/443, 441, 436, 489, 456; 514/280, 284, 395, 398

(56) References Cited

U.S. PATENT DOCUMENTS 4,701,458 * 10/1987 Greenberg .......................... 514/280
5,432,187 * 7/1995 Gazzard ............................. 514/388

OTHER PUBLICATIONS

Yamashita et al., *Chemical Abstracts*, vol. 111, #120904, 1989.*
Purohit et al., *Chemical Abstracts*, vol. 73, #2542, 1970.*
*The Merck Manual*, Robert Berkow, ed., Merck & Co., p. 158, 1977.*
Use of Berberine in Treatment of Giardiasis, S. Gupte MD., American Journal of Diseases of Children, 1975, p. 866.*
Combined Action of Antiamoebic Drugs and Antibiotics on Axenically Grown Entomoeba Histolytica.*
Yadava, et al., Division of Microbiology, Central Drug Research Institute, Lucknow, 1973, pp. 971–975.*
Bergerine in Giardiasis, Choudhry et al, Indian Pediatrics, 1972, pp. 143–146.*
Effects of Berberine, a Plant Alkaloid, on the Growth of Anaerobic Protozoa in Axenic Culture, Kaneda et al., The Tokai Journal of Experimental and Clinical Medicine, 1990, pp. 417–423.*

* cited by examiner

*Primary Examiner*—James M. Spear
(74) *Attorney, Agent, or Firm*—Schnader Harrison Segal & Lewis LLP

(57) ABSTRACT

A method for the treatment or prevention of chronic diarrhea caused by protozoa, especially microsporidia and cryptosporidia, in a patient is disclosed which method comprises administering to the patient an effective amount of a berberine alkaloid. The administration of the berberine alkaloid may be in combination with one or more antiprotozoal agents other than berberine.

38 Claims, No Drawings

BERBERINE ALKALOIDS AS A TREATMENT FOR CHRONIC PROTOZOALLY INDUCED DIARRHEA

This application is a continuation in part of pending provisional application Ser. No. 60/019,821, filed Jul. 3, 1996.

BACKGROUND

Diarrhea is generally described according to several criteria: duration (acute vs. chronic), clinical description (frequency, water content, presence of blood), and etiology. Chronic diarrhea has been described as two to three or more loose or watery stools per day for a period of at least 30 days.

It is important to distinguish chronic diarrhea from acute diarrhea. Chronic diarrhea is a distinct clinical entity from acute diarrhea that, if unchecked, results in morphological and functional pathology in the intestine. As opposed to acute diarrhea, histological examination of the chronically infected small intestinal mucosa reveals villus atrophy, crypt hypertrophy, and decreased mitosis. Chronic diarrhea leads to malabsorption, weight loss and cachexia. Both the World Health Organization (WHO) and the Center for Disease Control (CDC) have recognized this condition as the "Diarrhea Wasting Syndrome".

It is often possible to trace the cause of the clinical symptoms of chronic diarrhea in immunosuppressed patients to one or more organisms found in the intestinal tract. In these immunosuppressed individuals, microbes which are relatively harmless to the normal individual take advantage of the very weak immune response to establish a persistent opportunistic infective state. For example, in immunosuppressed patients, such as those with Acquired Immunodeficiency Syndrome (AIDS), chronic diarrhea has been ascribed to the presence of the HIV virus itself, to cytomegalovirus, to the presence of various toxic bacteria, and frequently to infection by pathogenic protozoa. Prevalent among the pathogenic protozoa associated with the presence of diarrhea in immunosuppressed patients are intracellular microsporidia and cryptosporidia (Goodgame, R. W. Ann. Int. Med. 124:429–441 (1996)). In healthy individuals, microsporidial and cryptosporidial infections are self-limiting but immunosuppressed patients can not mount an effective enough immune response to eliminate the causative organism.

Successful clinical management of chronic diarrhea in immunosuppressed patients requires control of the symptoms as well as elimination of the causal pathogen. The lack of effective treatment for the symptoms and causes of chronic diarrhea is a long recognized problem for which no completely satisfactory answer exists. Therapies which may be sufficient to treat acute diarrhea may be ineffective in the treatment of chronic diarrhea. Any benefit from these therapies may be short-lived or may produce adverse side effects with chronic administration. Currently there are no completely effective therapies for immunosuppressed patients with chronic diarrhea, particularly those associated with microsporidiosis or cryptosporidiosis.

This lack of effective therapy is particularly important in the case of cryptosporidiosis as the diarrhea is usually quite severe and often requires hospitalization and rehydration therapy to overcome dehydration and electrolyte imbalance. Cryptosporidiosis caused by *Cryptosporidium parvum* has been treated with the aminoglycoside antibiotic, paromomycin. However relapse after cessation of treatment is common. The somatostatin analog, octreotide (Wittner et al., Parasitic Diseases, vol. 7(3): 569–586 (1993)), has been reported to control the voluminous gastrointestinal secretion caused by cryptosporidia in AIDS patients, but diarrhea promptly returns following cessation of treatment.

Albendazole has been reported to temporarily relieve the diarrhea of some AIDS patients infected with microsporidia. Blanshard et al. (AIDS, vol. 6:311–313 (1992)) reported that albendazole was effective in resolving the chronic diarrhea of six AIDS patients with microsporidiosis caused by *Enterocytozoon bieneusi*. Albendazole appeared to cause degenerative changes in the parasite, but no significant reduction in parasite load was observed after oral treatment. Four of five patients relapsed within one month, and the fifth patient relapsed within two months. Blanshard et al. (J. Clin. Pathol. 46:898–902 (1993)) described the remission of diarrhea in 70% of 18 AIDS patients treated for microsporidiosis with albendazole, this time accompanied by a reduction in parasite load in those patients who responded. Albendazole was reported to slow the rate of parasite reproduction by interfering with tubulin polymerization. The drug did not completely arrest development, however, and the authors speculated that some strains might be partially resistant. Dieterich et al. (J. Infectious Diseases, vol. 169:178–183 (1994)) confirmed that albendazole improved symptoms and reduced the parasite burden in some of their 29 patients infected with *E. bieneusi*. However, following treatment, small bowel biopsies revealed that *E. bieneusi* spores were still present.

Another microsporidial species, *Encephalitozoon intestinalis* (formerly *Septata intestinalis*), infects macrophages as well as enterocytes and therefore can disseminate to different organs. Molina et al. (J. Infectious Diseases, 171:245–249 (1995)) reported that, although albendazole was initially effective in clearing *E. intestinalis* from the stools of the five AIDS patients they studied, relief was only temporary. Spores of *E. intestinalis* were again detected in stools from two of four patients followed for more than one month. Relapse occurred in one patient while receiving maintenance therapy with albendazole.

Berberine (5,6-Dihydro-9,10-dimethoxybenzo[g]-1,3-benzodioxolo[5,6-a]quinolizinium) is an alkaloid present in various species of Berberis and several other plant families. Oral berberine has both antisecretory and antimicrobial properties and is nontoxic at high doses.

For many centuries, berberine extract from plants has been used by traditional practitioners in both India and China to manage a variety of medical conditions, including acute diarrhea. In the laboratory, berberine shows in vitro activity against the protozoa *Trichomonas vaginalis, Giardia lamblia, Entamoeba histolytica*, several of the protozoal strains which cause leishmaniasis, as well as several types of fungi and bacteria. In the clinical setting, berberine, purified as a hydrochloride, sulfate, or tannate salt, has been used to treat bacterial, fungal and some protozoal infections. Orally administered berberine has been shown to be a safe and effective agent against acute diarrhea, such as that caused by the protozoal pathogen *G. lamblia*. Healing of sores caused by cutaneous species of leishmanial parasites has been effected by intradermal administration of berberine. Berberine has also proven useful in the treatment of acute diarrhea induced by *Escherichia coli* and *Vibrio cholerae* toxins.

Other uses of various berberine are disclosed in Maroko, U.S. Pat. Nos. 5,153,178, 4,980,344, 4,749,708, and 4,761,417, each of which is incorporated herein by reference.

SUMMARY OF THE INVENTION

In one embodiment, the invention is a method for the treatment of chronic diarrhea caused by protozoa in a patient comprising administering to the patient an effective amount of a berberine alkaloid. The berberine alkaloid may be berberine hydrochloride. The protozoan causative agent of the chronic diarrhea is frequently a microsporidial species, such as *Enterocytozoon bieneusi*, or a cryptosporidia. The method of the invention is particularly well suited for the treatment of protozoally caused chronic diarrhea in immunosuppressed patients, particularly those patients infected with the human immunodeficiency virus (HIV) and suffering from Acquired Immunodeficiency Syndrome (AIDS). The method of the invention is suited for treatment of immunosuppressed patients not infected with the HIV virus, for example patients receiving immunosuppressive medications. The method of the invention is also suitable for treatment of protozoally induced chronic diarrhea in non-immunosuppressed patients, both HIV-infected and HIV-free.

It is contemplated that the method of the invention is suitable for treatment of protozoally induced chronic diarrhea in humans and in veterinary patients, including mammals such as dogs, cats, ferrets, horses, cattle, goats, sheep, pigs, and exotic mammalian species, as well as reptiles, amphibians, and birds.

In the method of the invention, a patient suffering from chronic diarrhea caused by protozoa, especially caused by microsporidia or cryptosporidia, is administered enterally an effective therapeutic amount of a berberine alkaloid. Suitable berberine alkaloids for the method of the invention include berberine, such as berberine hydrochloride, and all protoberberines, and their derivatives. In a preferred embodiment, the berberine alkaloid is berberine hydrochloride. Examples of protoberberines which are suitable for use in the method of the invention include, but are not limited to berberine, berberrubine, coreximine, tetrahydropalmatine, jatrorrhizine, 13-hydroxyberberine chloride, coralyne chloride, 7,8-dihydro-13-methylberberine, berberine acetone, 13-allylberberine, palmatine, and 13-benzylberberine. The berberines which are suitable for the method of the invention are referred to collectively in the specification as "berberine" or as "berberine alkaloid".

The berberine may be administered in any form acceptable for enteral administration. Suitable non-limiting forms for enteral administration include tablets, capsules, pastes, liquids, chewable wafers, and suppositories.

The berberine is to be administered for a time and in an amount effective to alleviate, either completely or partially, protozoally induced chronic diarrhea. The berberine may be administered in divided daily doses, bid, tid, or qid, for a sufficient period of time to result in the resolution or in the improvement of the signs and symptoms of the diarrhea. Preferably, the dosage is divided so that one third of the daily dose is administered three times a day, about every eight hours. Typically, the berberine is administered for at least 10 or 12 days, although a treatment of as few as 5 or 7 days may be sufficient. Following alleviation of clinical signs, treatment with the berberine may be continued for a period of a month or longer, or may be discontinued.

In a second embodiment, the invention is a method for the treatment of chronic diarrhea caused by protozoa in a patient, such as a human patient, comprising administering to the patient a combination therapy comprising an effective amount of a berberine alkaloid plus one or more additional antiprotozoal compounds or agents, such as albendazole or metronidazole. Such combination therapy may be achieved by simultaneous or sequential administration of antiprotozoal agents. Where the mechanism of action of berberine differs from that of other antiprotozoal agents, combination therapy is expected to be more effective than treatment with either antiprotozoal agent alone.

The combination therapy is effective in controlling the symptoms of chronic protozoal diarrhea in non-immunosuppressed and in immunosuppressed patients, such as those patients infected with the HIV virus.

Another embodiment of the invention is a composition for the treatment or prevention of protozoally induced chronic diarrhea comprising a berberine alkaloid, such as berberine hydrochloride, and one or more additional antiprotozoal agents, such as albendazole or metronidazole, with a pharmaceutically acceptable carrier.

DETAILED DESCRIPTION OF THE INVENTION

The method of the invention comprises administering to a patient an effective amount of a berberine alkaloid, either alone or in combination with another antiprotozoal agent, in a dose effective for a period of time sufficient to reduce or alleviate the signs and symptoms of protozoally induced chronic diarrhea.

The method of the invention is typically used to treat chronic diarrhea which lasts for 30 days or more. However, the method of the invention may be used to treat chronic diarrhea of less than 30 days, such as for 7 to 10 days or less.

Preferably, the berberine is the hydrochloride of the berberine compound disclosed as compound 1169 in The Merck Index, 11th ed. (1989), incorporated herein by reference. Chemical names of berberine hydrochloride include 5,6-Dihydro-9,10-dimethoxybenzo[g]-1,3-benzodioxolo[5,6-a]quinolizinium hydrochloride and 7,8,13,13a-tetradehydro-9,10-dimethoxy-2,3-(methylenedioxy)berbinium hydrochloride.

Other berberines suitable for the method and composition of the invention include both natural and synthetic berberines and their derivatives, such as berberine, berberrubine, coreximine, tetrahydropalmatine, jatrorrhizine, 13-hydroxyberberine chloride, coralyne chloride, 7,8-dihydro-13-methylberberine, berberine acetone, 13-allylberberine, palmatine, and 13-benzylberberine. Additional berberines which are suitable for the method and composition of the invention include those disclosed in Shamma, M., "The Protoberberines and Retroprotoberberines", in The Isoquinoline Alkaloids: Chemistry and Pharmacology, Academic Press, Inc. (1972), which is attached hereto and expressly incorporated herein by reference. Other suitable berberines are disclosed in U.S. Pat. Nos. 5,153,178, 4,980,344, 4,749,708, and 4,761,417.

The amount of berberine to be administered to the patient may vary according to the patient and according to the particular berberine alkaloid used. In the case of berberine hydrochloride, the dosage is typically about 300 to 1500 mg per day. Preferably, the dosage of berberine hydrochloride is about 450 to 900 mg per day.

Preferably, the berberine is administered for a period from 14 to 21 days, typically about 14 days, although treatment may be for a period of a month or longer. The berberine is preferably administered for a time sufficient to result in the total eradication of the signs and symptoms of chronic diarrhea. In many cases, however, total elimination of chronic diarrhea may not be feasible and the berberine is administered for a time sufficient to result in the amelioration of the signs and symptoms of chronic diarrhea.

As stated previously, the chronic diarrhea which is suited to treatment by the method of the invention is caused by a protozoa. In a preferred embodiment, the causative agent is a microsporidium or a cryptosporidium. Other protozoal chronic diarrheas, such as those caused by *Entamoeba histolytica, Blastocystis hominis, Dientamoeba fragilis, Giardia lamblia, Balantidium coli, Isospora belli,* or *Cyclospora cayetanensis,* may be treated by the method of the invention.

The following examples are illustrative of the invention and are not meant to be limiting. For example, it is conceived that results of therapy in HIV infected patients in the following examples is indicative of results of therapy in immunosuppressed patients who are not HIV infected. Likewise, results of therapy in immunosuppressed but non-HIV infected patients is indicative of results in HIV infected patients. It will be evident to one skilled in the art that the treatments illustrated can be modified while being within the scope and contemplation of the invention.

EXAMPLE 1

In Vitro Effects of Berberine on Extracellular and Intracellular Protozoan Parasites The growth inhibitory activity of berberine hydrochloride in in vitro cultures of 4 protozoan parasites was demonstrated. The protozoa tested were established strains of 3 extracellular protozoan parasites; (1) *Giardia lamblia*, (2) *Trichomonas vaginalis*, (3) *Entamoeba histolytica*, and the intracellular microsporidian parasite (4) *Encephalitozoon intestinalis*.

Culture conditions and media for (1)–(3) and methods for assaying drug susceptibility were as described in Katiyar, S K and Edlind T D, Enhanced Antiparasitic Activity of Lipophilic Tetracyclines: Role of Uptake, *Antimicrob. Agents Chemother.*, vol. 35:2198–2202 (1991), incorporated herein by reference.

Cultures of the extracellular parasites were started from frozen stocks and passaged several times over a 2–3 week period to ensure viability, maximal growth rate, and lack of contamination. On day 1 of the assay, log phase cultures were diluted to $5 \times 10^4$ cells/ml in fresh medium and aliquoted to 2 ml vials, which were filled to maintain anaerobic conditions. The berberine was dissolved and diluted in water to various concentrations and then added to the cultures. "negative controls" received the vehicle alone.

Cultures were incubated at 37° C. with slow rotation. After 48 hours (for *T. vaginalis* and *G. lamblia*) and 72 hours (for *E. histolytica*), cell numbers were determined using a hemocytometer. The concentration of compound inhibiting growth 50% ($IC_{50}$) relative to controls was estimated from dose response plots. The assays were repeated at least twice.

Initially, the berberine was tested over a wide range of concentrations (0.1, 1, 10, 100 and 1000 μg/ml). Based on these results, the assays were repeated over a more narrow range of concentrations in duplicate, to both confirm the results and more precisely define the inhibitory concentrations.

Cultures of *E. intestinalis* infected African green monkey kidney (Vero) cells were kindly provided by G. S. Visvesvara, CDC, Atlanta, Ga. The *E. intestinalis* was originally isolated from the urine of an AIDS patient (J. Clin. Microbiol. 33:930–936, 1995).

Cells were grown in T25 flasks at 37° C. in a humidified $CO_2$ incubator, and subcultured when confluent (every 3–4 days). The medium was MEM supplemented with Earle's salts, L-glutamine, 5% heat-inactivated fetal bovine serum, fungizone (2 μg/ml) and gentamicin (50 μg/ml). *E. intestinalis* spores were prepared by centrifugation of infected cell medium (3–4 days old) at 2000×g for 15 min, followed by suspension in fresh medium to give $1-20 \times 10^4$ spores/ml (determined with a hemocytometer). These spores were used to infect new cultures (at a ratio of approximately 3 spores per Vero cell); this passaging was repeated every 2–3 weeks to maintain a high rate of spore infectivity.

Assays were performed in 24 well culture plates. Uninfected Vero cell monolayers in T25 flasks were detached by standard trypsin-EDTA treatment, centrifuged at 500×g for 10 min, and cell pellets were resuspended in fresh medium to $5 \times 10^4$ cell/ml. One ml was placed in each well and incubated 12–15 h. The medium was removed and replaced with 1 ml of medium containing freshly isolated *E. intestinalis* spores (3–4 spores/cell). Berberine hydrochloride was then added at a concentration of 3, 10, 30 or 100 μl, dissolved in water at 1 mg/ml with heating to approximately 60° C. Control wells received corresponding volumes of vehicle alone.

Every 72–96 h after infection, the medium was completely removed, discarded, and replaced with fresh medium plus berberine. The medium from the 4th change (2–3 weeks post infection) was collected into tubes and spore numbers were determined in a hemocytometer. The spores present in this medium were derived from productively infected cells only, since residual spores from the original inoculum were largely eliminated by the repeated medium changes. Consequently, spore numbers after 3–4 medium changes provided a quantitative measure of the effects of berberine on microsporidia growth.

The results of the in vitro assays are shown in Tables 1 and 2 below.

TABLE I

Growth of *G.lamblia, T.vaginalis* and *E.histolytica* in the presence of berberine hydrochloride.

|  | G.lamblia % growth | | | T.vaginalis % growth | | | E.histolytica % growth | |
| --- | --- | --- | --- | --- | --- | --- | --- | --- |
|  | Exp. 1 | Exp. 2 | Exp. 3 | Exp. 1 | Exp. 2 | Exp. 3 | Exp. 1 | Exp. 2 |
| Berberine (μg/ml) | | | | | | | | |
| 0 | 100 | 100 | 100 | 100 | 100 | 100 | 100 | 100 |
| 30 | 99 | 97 | ND | 93 | 99 | 96 | 102 | 101 |
| 62 | 89 | 85 | 88 | 90 | 98 | 98 | ND | 90 |
| 125 | 79 | 69 | 75 | 59 | 60 | 60 | 100 | 101 |
| 250 | 63 | 59 | 52 | 20 | 28 | 45 | ND | 101 |
| 500 | 40 | 44 | 32 | 2 | 3 | 22 | 100 | 96 |
| 1000 | 9 | 20 | 5 | 1 | 1 | 6.8 | 72 | 76 |
| $IC_{50}$ (μg/ml) | 350 | | | 170 | | | >1000 | |

TABLE 2

Growth of the microsporidium E. intestinalis in the presence of berberine hydrochloride.

| Concentration of Berberine (μg/ml) | % growth |
| --- | --- |
| 0 (control) | 100 |
| 3 | 81 |
| 10 | 13 |
| 30 | 8 |
| 100 | 1.7 |

$IC_{50} = 5.5$ μg/ml

As shown by the data in Tables 1 and 2, berberine is an effective antiprotozoal agent against a broad range of protozoa, as determined by in vitro assay. It is particularly noteworthy that the berberine hydrochloride showed activity against the microsporidium *E. intestinalis*.

EXAMPLE 2

Human Clinical Trials versus Microsporidia

Seventy-five (75) HIV infected patients, 18 years of age or older, presenting with chronic diarrhea caused by microsporidia, are selected. Presence of the microsporidial parasite is determined by small bowel biopsy and transmission electron microscopy (TEM). Blood specimens are evaluated to confirm that each patient is HIV seropositive.

Each patient is randomly assigned to one of three groups of 25 patients. Group I receives berberine hydrochloride 450 mg, daily, administered orally in divided doses of 150 mg tid ("low dose"); Group II receives berberine hydrochloride 900 mg, daily, administered orally in divided doses of 300 mg tid ("high dose"); and Group III receives a placebo, administered orally, tid. Each member of each group receives its treatment for 14 (+/−2) days.

Patients are clinically evaluated by a physician before the initiation of therapy and after 7 (+/−1) days and 14 (+/−2 days) after initiation of therapy. Patients are again evaluated at 14 (+/−2) days and at two months after cessation of therapy. At each evaluation, the patients are physically examined, weighed, and clinical laboratory tests, including CBC with differential, urinalysis, and blood chemistries (creatinine, SAP, SGPT, SGOT, LDH, bilirubin, total protein, albumin, glucose, calcium, sodium, potassium, bicarbonate, chloride, GGT, creatinine kinase) are performed. At the 7 and 14 day visits after initiation of therapy, if the condition of the patient has worsened or has not improved, the patient may be withdrawn from the study.

Patient response is identified as either 1) "cured", complete resolution of signs and symptoms of diarrhea, 2) "improved", improvement, but incomplete resolution of the signs and symptoms of diarrhea, 3) "no change", no difference in the signs and symptoms of diarrhea, or 4) "worse", worsening of the signs and symptoms of diarrhea. A response at the 14 day evaluation after initiation of therapy of "cured" or "improved" is considered a treatment success whereas a response of "no change" or "worse" is considered a treatment failure.

Additional evaluation parameters between treatment groups are weight gain or cessation of weight loss and presence or absence of recurrence of diarrhea at the 14 day and 2 month post treatment evaluation. Patients are also evaluated for the absence or presence of viable protozoal organisms in stool.

Compared to placebo controls, berberine treated patients, in both the low and high dose groups, have significantly improved clinical symptoms, and laboratory parameters. Additionally, patients receiving berberine report a subjective improved quality of life compared to controls.

EXAMPLE 3

Human Clinical Trials versus Cryptosporidia

The protocol of Example 2 is repeated in 75 additional HIV seropositive patients suffering from chronic diarrhea except that a cryptosporidial parasite is identified in each patient.

Results are similar to results of Example 2.

EXAMPLE 4

Human Clinical Trials versus *E. intestinalis*

The protocol of Example 2 is repeated in 75 additional HIV seropositive patients suffering from chronic diarrhea except that *E. intestinalis* is identified in each patient.

Results are similar to results of Example 2.

EXAMPLE 5

Protoberberines in a Hamster Animal Model

Ten hamsters suffering from chronic diarrhea caused by microsporidia are randomized into two groups of 5 hamsters. One group receives the protoberberine palmatine and the second group receives the protoberberine dihydroberberine. The protoberberines are administered orally at a dose rate of 52 mg/kg/day for ten (10) days.

After 10 days of treatment, the condition of the hamsters in both groups is improved and none of the hamsters have diarrhea. An intestinal biopsy following therapy does not reveal the presence of microsporidia.

EXAMPLE 6

Protoberberines in a Mouse Animal Model

Ten mice suffering from chronic diarrhea caused by microsporidia are randomized into two groups of 5 mice. One group receives the protoberberine palmatine and the second group receives the protoberberine jatrorrhizine. The protoberberines are administered orally at a dose rate of 52 mg/kg/day for ten (10) days.

After 10 days of treatment, the condition of the mice in both groups is improved and none of the mice have diarrhea. An intestinal biopsy following therapy does not reveal the presence of microsporidia.

EXAMPLE 7

Prophylactic Use of Berberines

Twenty five (25) HIV infected patients, 18 years of age or older, not presenting with chronic diarrhea, are selected. Blood specimens are evaluated to confirm that each patient is HIV seropositive.

Each of the twenty five (25) patients receives a treatment with berberine according to the low dose of Example 2 for a period of two months. None of the patients develops diarrhea during the treatment and all of the patients tolerate the treatment well with no or minimal adverse reactions to the medication.

EXAMPLE 8

Maintenance Use of Berberines

Ten (10) patients from Group I and ten (10) patients from Group II of Example 2 are maintained on a continued low dose or high dose regimen, respectively, of berberine following an initial treatment period of two weeks resulting in a cure of the chronic diarrhea. The patients remain on treatment for periods ranging from two to six months. No recurrence of chronic diarrhea is reported in either group.

EXAMPLE 9

Combination Antivrotozoal Therapy

Twenty five (25) HIV infected patients, 18 years of age or older, presenting with chronic diarrhea caused by microsporidia, are selected. Presence of the microsporidial parasite is determined by small bowel biopsy and transmission electron microscopy (TEM). Blood specimens are evaluated to confirm that each patient is HIV seropositive.

Each patient receives therapy according to the low dose of Example 2 for a period of two weeks. Concurrently, twelve (12) of the patients receive a two-week regimen of albendazole at a dose of 400 mg, 2 times daily, and thirteen (13) of the patients receive a two-week regimen of metronidazole at a dose of 500 mg, 3 times daily.

Following therapy, the patients show significantly improved clinical symptoms, and laboratory parameters. Additionally, patients receiving the combination therapy of berberine/albendazole or berberine/metronidazole report an improved quality of life compared to untreated controls.

EXAMPLE 10

Combination Antiprotozoal Therapy

Twenty four (24) HIV infected patients, 18 years of age or older, presenting with chronic diarrhea caused by microsporidia, are selected. Presence of the microsporidial parasite is determined by small bowel biopsy and transmission electron microscopy (TEM). Blood specimens are evaluated to confirm that each patient is HIV seropositive.

Each patient receives one of the following therapy regimens for a period of two weeks. Four (4) of the patients receive tid a composition containing a combination of albendazole and berberine hydrochloride in a dosage of 400 mg of albendazole and 150 mg of berberine hydrochloride. Four (4) of the patients receive tid 400 mg of albendazole followed by 150 mg berberine hydrochloride. Four (4) of the patients receive tid 150 mg berberine hydrochloride followed by 400 mg of albendazole. Four (4) of the patients receive tid a composition containing a combination of metronidazole and berberine hydrochloride in a dosage of 500 mg of metronidazole and 150 mg of berberine hydrochloride. Four (4) of the patients receive tid 500 mg of metronidazole followed by 150 mg of berberine hydrochloride. Four (4) of the patients receive tid 150 mg of berberine hydrochloride followed by 500 mg of metronidazole.

Following therapy, the patients in each of the groups show significantly improved clinical symptoms, and laboratory parameters. Additionally, patients receiving the combination therapy of berberine/albendazole or berberine/ metronidazole report an improved quality of life compared to untreated controls, wherein either the antiprotozoal agents are given simultaneously, berberine is given following the other antiprotozoal agent, or berberine is given before the other antiprotozoal agent.

The invention is not intended to be limited to the precise embodiments described herein but includes all modifications encompassed within the scope and spirit of the following claims.

What is claimed is:

1. A method for the treatment or alleviation of symptoms of protozoally induced chronic diarrhea in a patient comprising administering to the patient an effective amount of a berberine alkaloid, and continuing the administration for a sufficient time to substantially alleviate the chronic diarrhea is induced by protozoa selected from the group consisting of Microsporridia spp. and Cryptospordia spp.

2. The method of claim 1 wherein the berberine alkaloid is selected from the group consisting of berberine hydrochloride, berberine, berberrubine, coreximine, tetrahydropalmatine, jatrorrhizine, 13-hydroxyberberine chloride, coralyne chloride, 7,8-dihydro-13-methylberberine, berberine acetone, 13-allylberberine, palmatine, and 13-benzylberberine.

3. The method of claim 1 wherein the berberine alkaloid is berberine hydrochloride.

4. The method of claim 1 wherein the administration is enteral.

5. The method of claim 1 wherein the alleviation of symptoms of chronic diarrhea is characterized by the absence of Microsporidia.

6. The method of claim 1 wherein the patient is a human patient.

7. The method of claim 1 wherein the patient is immunosuppressed.

8. The method of claim 6 wherein the patient is infected with human immunodeficiency virus.

9. The method of claim 1 wherein the patient is a veterinary patient.

10. A composition for the treatment or alleviation of symptoms of chronic diarrhea induced by protozoa selected from the group consisting of *Blastocystis hominis, Dientamoeba fragilis, Balantinium coli, Isopora belli,* and *Cylclospora cayetanensis,* comprising a berberine alkaloid and a pharmaceutically acceptable carrier.

11. The method of claim 1 wherein an antiprotozoal agent is administered prior to, subsequent to, or concurrently with the berberine alkaloid.

12. The method of claim 11 wherein the antiprotozoal agent is albendazole or metronidazole.

13. A composition for the treatment or alleviation of symptoms of protozoally induced chronic diarrhea in a patient comprising a berberine alkaloid selected from the group consisting of berberine and berberine hydrochloride, an antiprotozoal agent selected from the group consisting of albendazole and metronidazole, and a pharmaceutically acceptable carrier, wherein said diarrhea is induced by protozoa selected from the group consisting of Microsporidia spp. and Cryptosporidia spp.

14. A composition for the treatment or alleviation of symptoms of protozoally induced chronic diarrhea in a patient comprising a berberine alkaloid selected from the group consisting of berberrubine, coreximine, tetrahydropalmatine, jatrorrhizine, 13-hydroxyberberine chloride, coralyne chloride, 7,8-dihydro-13-methylberberine, berberine acetone, 13-allylberberine, palmatine, and 13-benzylberberine; an antiprotozoal agent selected from the group consisting of albendazole and metronidazole; and a pharmaceutically acceptable carrier, wherein said diarrhea is induced by protozoa selected from the group consisting of Microsporidia spp. and Cryptosporidia spp.

15. The composition of claim 13 wherein the antiprotozoal agent is metronidazole.

16. The composition of claim 14 wherein the antiprotozoal agent is metronidazole.

17. The method of claim 1 in which the protozoa are *Enterocytozoon bieneusi, Encephalitozoon intestitnalis* or *Cryptosporidium parvum.*

18. The method of claim 8 in which the protozoa are *Enterocytozoon bieneusi, Encephalitozoon intestinalis* or *Cryptosporidium parvum.*

19. The method of claim 12 in which the antiprotozoal agent is albendazole.

20. The composition of claim 13 in which the antiprotozoal agent is albendazole.

21. The composition of claim 14 in which the antiprotozoal agent is albendazole.

22. A method for the treatment or alleviation of symptoms of protozoally induced chronic diarrhea in a patient comprising administering to the patient an effective amount of a berberine alkaloid, and continuing the administration for a sufficient time to substantially alleviate the chronic diarrhea is induced by protozoa selected from the group consisting of *Blastocystis hominis, Dientamoeba fragilis Balantidium coli, Isoipora belli*, and *Cyclospora cayetanensis*.

23. The composition of claim 13 or 14 wherein the alleviation of symptoms of chronic diarrhea is characterized by the absence of Microsporidia.

24. The composition of claim 13 or 14 in which the protozoa are Microspordia spp.

25. The composition of claim 24 in which the Microsporidia spp. are *Encephalitozoon intestinalis*.

26. The composition of claim 13 or 14 in which the protozoa are Cryptosporidia spp.

27. The composition of claim 13 in which the berberine alkaloid is berberine hydrochloride.

28. The method of claim 1 in which berberine alkaloid is administered at a dosage of about 300 to about 1500 mg per day.

29. The method of claim 28 in which the dosage is about 450 to about 900 mg per day.

30. The method of claim 1 in which the patient is non-immunosuppressed.

31. A composition for the treatment or alleviation of symptoms of protozoally induced chronic diarrhea induced by Microsporidia spp. or Cryptosporidia spp. in a patient comprising a berberine alkaloid selected from the group consisting of berberine and berberine hydrochloride and a pharmaceutically acceptable carrier.

32. A composition for the treatment or alleviation of symptoms of protozoally induced chronic diarrhea induced by Microsporidia spp. or Cryptosporidia spp. in a patient, comprising a berberine alkaloid selected from the group consisting of berberrubine, coreximine, tetrahydropalmatine, jatrorrhizine, 13-hydroxyberberine chloride, coralyne chloride, 7,8-dihydro-13-methylberberine, berberine acetone, 13-allylberberine, palmatine, and 13-benzylberberine.

33. The composition of claim 31 in which the berberine alkaloid is berberine hydrochloride.

34. The composition of claim 31 or 32 in which the protozoa are *Enterocytozoon bieneusi, Encephalitozoon intestinalis* or *Cryptosporidium parvum*.

35. The composition of claim 31 or 32 in which the protozoa are Microsporidia spp.

36. The composition of claim 35 in which the Microsporidia spp. are Encephalitizoon intestinialis.

37. The composition of claim 31 or 32 in which the protozoa are Cryptosporidia spp.

38. The composition of claim 13, wherein said berberine alkaloid is berberine.

\* \* \* \* \*